(12) United States Patent
Kutukova et al.

(10) Patent No.: US 8,034,767 B2
(45) Date of Patent: Oct. 11, 2011

(54) **METHOD FOR PRODUCING PURINE NUCLEOSIDES AND NUCLEOTIDES BY FERMENTATION USING A BACTERIUM BELONGING TO THE GENUS *ESCHERICHIA* OR *BACILLUS***

(75) Inventors: Ekaterina Aleksandrovna Kutukova, Moscow (RU); Natalia Pavlovna Zakataeva, Moscow (RU); Vitaly Arkadievich Livshits, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/476,476

(22) Filed: Jun. 2, 2009

(65) Prior Publication Data

US 2009/0298127 A1 Dec. 3, 2009

Related U.S. Application Data

(63) Continuation of application No. PCT/JP2007/074195, filed on Dec. 11, 2007.

(30) Foreign Application Priority Data

Dec. 22, 2006 (RU) ................ 2006145713

(51) Int. Cl.
 *C07H 19/00* (2006.01)
 *A61K 38/00* (2006.01)
(52) U.S. Cl. ............ 514/2; 530/350; 435/410; 435/170; 536/28.1; 536/55.3; 536/27.1
(58) Field of Classification Search .................. None
 See application file for complete search history.

(56) References Cited

U.S. PATENT DOCUMENTS

| | | | |
|---|---|---|---|
| 3,575,809 A | 4/1971 | Shiro et al. | |
| 3,736,228 A | 5/1973 | Nakayama et al. | |
| 3,912,587 A | 10/1975 | Enei et al. | |
| 3,960,660 A | 6/1976 | Enei et al. | |
| 3,960,661 A | 6/1976 | Enei et al. | |
| 5,756,315 A * | 5/1998 | Mori et al. | 435/89 |
| 6,887,691 B2 | 5/2005 | Livshits et al. | |
| 6,960,455 B2 | 11/2005 | Livshits et al. | |
| 6,979,560 B1 * | 12/2005 | Livshits et al. | 435/107 |
| 7,138,266 B2 | 11/2006 | Debabov et al. | |
| 7,179,623 B2 | 2/2007 | Livshits et al. | |
| 7,259,003 B2 | 8/2007 | Livshits et al. | |
| 7,399,617 B1 | 7/2008 | Livshits et al. | |
| 7,435,560 B1 | 10/2008 | Matsui et al. | |
| 7,524,656 B2 | 4/2009 | Livshits et al. | |
| 7,527,950 B2 | 5/2009 | Livshits et al. | |
| 7,531,332 B2 | 5/2009 | Livshits et al. | |
| 2005/0239177 A1 | 10/2005 | Livshits et al. | |
| 2008/0241888 A1 | 10/2008 | Zakataeva et al. | |

FOREIGN PATENT DOCUMENTS

| | | |
|---|---|---|
| EP | 0 286 303 | 10/1988 |
| EP | 0 393 969 | 10/1990 |
| EP | 0 465 132 | 1/1992 |
| EP | 0 612 688 | 8/1994 |
| EP | 1004663 | 5/2000 |
| EP | 1016710 | 7/2000 |
| EP | 0 272 660 | 6/2008 |
| JP | 38-23099 | 10/1938 |
| JP | 54-17033 | 6/1979 |
| JP | 55-2956 | 1/1980 |
| JP | 55-45199 | 11/1980 |
| JP | 57-14160 | 3/1982 |
| JP | 57-41915 | 9/1982 |
| JP | 58-17592 | 4/1983 |
| JP | 58-158197 | 9/1983 |
| JP | 58-175493 | 10/1983 |
| JP | 59-028470 | 2/1984 |
| JP | 59-042895 | 3/1984 |
| JP | 60-156388 | 8/1985 |
| JP | 63-248394 | 10/1988 |
| JP | 64-027477 | 1/1989 |
| JP | 01-174385 | 7/1989 |
| JP | 03-058787 | 3/1991 |
| JP | 03-164185 | 7/1991 |
| JP | 05-084067 | 4/1993 |
| JP | 05-192164 | 8/1993 |
| JP | 2003-219876 | 8/2003 |
| RU | 2239656 | 8/2003 |
| RU | 2244003 | 1/2005 |
| RU | 2244004 | 1/2005 |
| RU | 2271391 | 3/2005 |
| WO | WO99/03988 | 1/1999 |
| WO | WO2005/023850 | 3/2005 |
| WO | WO 2008/084629 | 7/2008 |

OTHER PUBLICATIONS

Aleshin, V. V., "A new family of amino-acid-efflux proteins," TIBS 1999;24:133-135.
Kotani, Y., et al., "Inosine Accumulation by Mutants of *Brevibacterium ammoniagenes* Strain Improvement and Culture Conditions," Agric. Biol. Chem. I978;42(2):399-405.
Pao, S. S., et al., "Major Facilitator Superfamily," Microbiol. Molecular Biol. Rev. 1998;62(1):1-34.
Paulsen, I. T., et al., "Microbial Genome Analyses: Global Comparisons of Transport Capabilities Based on Phylogenies, Bioenergetics and Substrate Specificities," J. Mol. Biol. 1998;573-592.
Saier, M. H., et al., "The Major Facilitator Superfamily," J. Mol. Microbiol. Biotechnol. 1999;1(2):257-279.
Written Opinion of The International Searching Authority for PCT Patent App. No. PCT/JP2007/074195 (Jul. 2, 2009).
Kutukova, E. A., et al., "The yeaS (leuE) gene of *Escherichia coli* encodes an exporter of leucine, and the Lrp protein regulates its expression," FEBS Letters 2005;579:4629-4634.

(Continued)

*Primary Examiner* — Anand Desai
*Assistant Examiner* — Samuel Liu
(74) *Attorney, Agent, or Firm* — Shelly Guest Cermak; Cermak Nakajima LLP

(57) ABSTRACT

A method is provided for producing a purine nucleoside, such as inosine and guanosine, and a method for producing a 5'-purine nucleotide such as 5'-inosinic acid or 5'-guanylic acid, using a bacterium belonging to the either genus *Escherichia* or genus *Bacillus*, wherein purine nucleoside productivity of said bacterium is enhanced by enhancing an activity of a protein encoded by the yeaS (leuE) gene.

10 Claims, 1 Drawing Sheet

OTHER PUBLICATIONS

Zakataeva, N. P., et al., "Export of Metabolites by the Proteins of the DMT and RhtB Families and Its Possible Role in Intercellular Communication," Microbiol. 2006;75(4):438-448.

International Search Report and Written Opinion of The International Searching Authority for PCT Patent App. No. PCT/JP2007/074195 (Jun. 12, 2008).

Non-Final Office Action issued in U.S. Appl. No. 09/466,935 on Mar. 9, 2009.

Latest Amendment and Response filed in U.S. Appl. No. 09/466,935 on Apr. 2, 2008.

* cited by examiner

SEQUENCE LISTING

<160> NUMBER OF SEQ ID NOS: 6

<210> SEQ ID NO 1
<211> LENGTH: 639
<212> TYPE: DNA
<213> ORGANISM: Escherichia coli
<220> FEATURE:
<221> NAME/KEY: CDS
<222> LOCATION: (1)..(639)

<400> SEQUENCE: 1

```
gtg ttc gct gaa tac ggg gtt ctg aat tac tgg acc tat ctg gtt ggg       48
Val Phe Ala Glu Tyr Gly Val Leu Asn Tyr Trp Thr Tyr Leu Val Gly
1               5                   10                  15 gcc att ttt att gtg ttg gtg cca ggg cca aat acc ctg ttt gta ctc       96
Ala Ile Phe Ile Val Leu Val Pro Gly Pro Asn Thr Leu Phe Val Leu
            20                  25                  30 aaa aat agc gtc agt agc ggt atg aaa ggc ggt tat ctt gcg gcc tgc      144
Lys Asn Ser Val Ser Ser Gly Met Lys Gly Gly Tyr Leu Ala Ala Cys
        35                  40                  45 ggt gta ttt att ggc gat gcg gta ttg atg ttt ctg gca tgg gct gga      192
Gly Val Phe Ile Gly Asp Ala Val Leu Met Phe Leu Ala Trp Ala Gly
    50                  55                  60 gtg gcg aca tta att aag acc acc ccg ata tta ttc aac att gta cgt      240
Val Ala Thr Leu Ile Lys Thr Thr Pro Ile Leu Phe Asn Ile Val Arg
65                  70                  75                  80 tat ctt ggt gcg ttt tat ttg ctc tat ctg ggg agt aaa att ctt tac      288
Tyr Leu Gly Ala Phe Tyr Leu Leu Tyr Leu Gly Ser Lys Ile Leu Tyr
                85                  90                  95 gcg acc ctg aag ggt aaa aat agc gag gcc aaa tcc gat gag ccc caa      336
Ala Thr Leu Lys Gly Lys Asn Ser Glu Ala Lys Ser Asp Glu Pro Gln
            100                 105                 110 tac ggt gct att ttt aaa cgc gcg tta att ttg agc ctg act aat ccg      384
Tyr Gly Ala Ile Phe Lys Arg Ala Leu Ile Leu Ser Leu Thr Asn Pro
        115                 120                 125 aaa gcc att ttg ttc tat gtg tcg ttt ttc gta cag ttt atc gat gtt      432
Lys Ala Ile Leu Phe Tyr Val Ser Phe Phe Val Gln Phe Ile Asp Val
    130                 135                 140
```

```
aat gcc cca cat acg gga att tca ttc ttt att ctg gcg gcg acg ctg    480
Asn Ala Pro His Thr Gly Ile Ser Phe Phe Ile Leu Ala Ala Thr Leu
145                 150                 155                 160 gaa ctg gtg agt ttc tgc tat ttg agc ttc ctg att ata tct ggt gct    528
Glu Leu Val Ser Phe Cys Tyr Leu Ser Phe Leu Ile Ile Ser Gly Ala
                165                 170                 175 ttt gtc acg cag tac ata cgt acc aaa aag aaa ctg gct aaa gtt ggc    576
Phe Val Thr Gln Tyr Ile Arg Thr Lys Lys Lys Leu Ala Lys Val Gly
            180                 185                 190 aac tca ctg att ggt ttg atg ttc gtg ggt ttc gct gcc cga ctg gcg    624
Asn Ser Leu Ile Gly Leu Met Phe Val Gly Phe Ala Ala Arg Leu Ala
        195                 200                 205 acg ctg caa tcc tga                                                 639
Thr Leu Gln Ser
    210
```

```
<210> SEQ ID NO 2
<211> LENGTH: 212
<212> TYPE: PRT
<213> ORGANISM: Escherichia coli

<400> SEQUENCE: 2

Val Phe Ala Glu Tyr Gly Val Leu Asn Tyr Trp Thr Tyr Leu Val Gly
1               5                   10                  15

Ala Ile Phe Ile Val Leu Val Pro Gly Pro Asn Thr Leu Phe Val Leu
            20                  25                  30

Lys Asn Ser Val Ser Ser Gly Met Lys Gly Gly Tyr Leu Ala Ala Cys
        35                  40                  45

Gly Val Phe Ile Gly Asp Ala Val Leu Met Phe Leu Ala Trp Ala Gly
    50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Leu Tyr Leu Gly Ser Lys Ile Leu Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
        115                 120                 125

Lys Ala Ile Leu Phe Tyr Val Ser Phe Phe Val Gln Phe Ile Asp Val
    130                 135                 140

Asn Ala Pro His Thr Gly Ile Ser Phe Phe Ile Leu Ala Ala Thr Leu
145                 150                 155                 160

Glu Leu Val Ser Phe Cys Tyr Leu Ser Phe Leu Ile Ile Ser Gly Ala
                165                 170                 175

Phe Val Thr Gln Tyr Ile Arg Thr Lys Lys Lys Leu Ala Lys Val Gly
            180                 185                 190

Asn Ser Leu Ile Gly Leu Met Phe Val Gly Phe Ala Ala Arg Leu Ala
        195                 200                 205

Thr Leu Gln Ser
    210

<210> SEQ ID NO 3
<211> LENGTH: 36
<212> TYPE: DNA
<213> ORGANISM: Artificial
<220> FEATURE:
<223> OTHER INFORMATION: primer 1

<400> SEQUENCE: 3
```

-continued

```
ctgagtcgac gtgttcgctg aatacggggt tctgaa                              36

<210> SEQ ID NO 4
<211> LENGTH: 31
<212> TYPE: DNA
<213> ORGANISM: Artificial
<220> FEATURE:
<223> OTHER INFORMATION: primer 2

<400> SEQUENCE: 4
gtctctagaa tcaggattgc agcgtcgcca g                                   31

<210> SEQ ID NO 5
<211> LENGTH: 70
<212> TYPE: DNA
<213> ORGANISM: Artificial
<220> FEATURE:
<223> OTHER INFORMATION: primer 3

<400> SEQUENCE: 5
tctttcctat aagcttgaaa aacaaagcat gagaaggtgg gaacagagtg ttcgctgaat    60
acggggttct                                                           70

<210> SEQ ID NO 6
<211> LENGTH: 39
<212> TYPE: DNA
<213> ORGANISM: Artificial
<220> FEATURE:
<223> OTHER INFORMATION: primer 4

<400> SEQUENCE: 6
acgtttaccc cggggcgggc tgaaagcatc aggattgca                           39
```

METHOD FOR PRODUCING PURINE NUCLEOSIDES AND NUCLEOTIDES BY FERMENTATION USING A BACTERIUM BELONGING TO THE GENUS *ESCHERICHIA* OR *BACILLUS*

This application is a continuation of PCT/JP2007/074195, filed Dec. 11, 2007, which claims priority under 35 U.S.C. §119 to Russian Patent Application No. 2006145713, filed on Dec. 22, 2006, which is incorporated in its entirety by reference. The Sequence Listing in electronic format filed herewith is also hereby incorporated by reference in its entirety (File Name: US-305_Seq_List; File Size: 6 KB; Date Created: Jun. 1, 2009).

BACKGROUND OF THE INVENTION

1. Technical Field

The present invention relates to a method for producing purine nucleosides, which are important as raw materials in the synthesis of 5'-purine nucleotides, such as 5'-inosinic acid or 5'-guanylic acid, and the present invention further relates to a novel microorganism used for the production.

2. Background Art

Conventionally, purine nucleosides, such as inosine, guanosine, and xanthosine, are industrially produced by fermentation utilizing adenine auxotrophic strains. Alternatively, such strains may be further imparted with drug resistance against various drugs, such as purine analogues and sulfaguanidine. These strains include those which belong to the genus *Bacillus* (Japanese Patent Publication Nos. 38-23099 (1963), 54-17033 (1979), 55-2956 (1980), and 55-45199 (1980), Japanese Patent Application Laid-Open No. 56-162998 (1981), Japanese Patent Publication Nos. 57-14160 (1982) and 57-41915 (1982), and Japanese Patent Application Laid-Open No. 59-42895 (1984)), or the genus *Brevibacterium* (*Corynebacterium*) (Japanese Patent Publication Nos. 51-5075 (1976) and 58-17592 (1972), and Agric. Biol. Chem., 42, 399 (1978)), or the genus *Escherichia* (WO9903988), and the like.

Typical methods for obtaining such mutant strains include subjecting microorganisms to mutagenesis by UV irradiation or by treating them with nitrosoguanidine (N-methyl-N'-nitro-N-nitrosoguanidine) and selecting the mutant strain by using a suitable medium. On the other hand, breeding such mutant strains using genetic engineering techniques has also been practiced for strains belonging to the genus *Bacillus* (Japanese Patent Application Laid-Open Nos. 58-158197 (1983), 58-175493 (1983), 59-28470 (1984), 60-156388 (1985), 1-27477 (1989), 1-174385 (1989), 3-58787 (1991), 3-164185 (1991), 5-84067 (1993), and 5-192164 (1993)), the genus *Brevibacterium* (*Corynebacterium*) (Japanese Patent Application Laid-Open No. 63-248394 (1988)), or the genus *Escherichia* (WO9903988).

The productivity of purine nucleoside-producing strains could be further improved by increasing the purine nucleoside excretion activity. It is generally accepted that the penetration of metabolites across the cytoplasmic membrane is usually mediated by specific efflux transporter proteins (Pao et al., Microbiol. Mol. Biol. Rev., 62, 1-34, (1998); Paulsen et al., J. Mol. Biol., 277, 573-592 (1998); Saier et al., J. Mol. Microbiol. Biotechnol., 257-279 (1999)). The present inventors have previously shown that inosine- or xanthosine-producing strains belonging to the genus *Escherichia* or *Bacillus* which have enhanced activity of the RhtA protein, coded by rhtA (ybiF) gene, produced more inosine or xanthosine than the parental strains (Russian patent No. 2239656). Besides, inosine-producing strains belonging to the genus *Escherichia* which have enhanced activity of the YijE, YdeD, or YicM proteins, coded by the yijE, ydeD or yicM genes, respectively, produced more inosine than the parental strains (Russian patent Nos. 2244003, 2244004, 2271391, respectively).

The present inventors have previously found that the yeaS (leuE) gene of *E. coli* encodes a membrane protein which belongs to the RhtB family and is involved in the efflux of amino acids (Aleshin et al., TIBS, 1999). Specifically, this gene encodes an exporter of leucine, histidine, and methionine (Kutukova et al., FEBS Letters, 579, 4629-4534, 2005).

SUMMARY OF THE INVENTION

It is an aspect of the present invention is to enhance the productivity of purine nucleosides by purine nucleoside-producing strains, and to provide a method for producing purine nucleosides using these strains.

This aspect was achieved by identifying the yeaS gene. This gene encodes a putative exporter of amino acids which imparts resistance to the purine base analogues, 8-azaadenine, 2,6-diaminopurine, 6-mercaptopurine, and 6-thioguanine, when introduced into a strain as a wild-type allele on a multi-copy vector. Furthermore, the yeaS gene can enhance purine nucleoside production when placed under the control of a constitutive promoter and introduced into the cells of a purine nucleoside-producing strain belonging to the genus *Escherichia* or genus *Bacillus*.

Thus, the present invention provides a microorganism belonging to the genus *Escherichia* or the genus *Bacillus* which has the ability to produce purine nucleosides.

Specifically, it is an aspect of the present invention to provide a microorganism that has improved purine nucleoside producing ability based on the increased activity of a protein that seems to be involved in the transport of purine nucleosides out of the microorganism. More specifically, it is an aspect of the present invention to provide a microorganism that has improved purine nucleoside producing ability based on increased expression of a gene coding for a protein involved in purine nucleoside excretion.

It is an aspect of the present invention to provide a method for producing a purine nucleoside by fermentation comprising culturing the aforementioned microorganism in a culture medium, and collecting the purine nucleoside from the medium.

It is a further aspect of the present invention to provide a method for producing a 5'-purine nucleotide such as 5'-inosinic acid or 5'-guanylic acid comprising cultivating the bacterium of the present invention in a culture medium, phosphorylating a purine nucleoside such as inosine or guanosine, and collecting the 5'-purine nucleotide.

It is an aspect of the present invention to provide an *Escherichia* or *Bacillus* bacterium having a purine nucleoside producing ability, wherein an activity of a protein is enhanced, the protein being selected from the group consisting of:

(A) a protein comprising the amino acid sequence shown in SEQ ID NO: 2; and (B) a protein comprising the amino acid sequence shown in SEQ ID NO: 2, wherein one or several amino acids are substituted, deleted, inserted, added, or inverted, and the protein has an activity of making the *Escherichia* or *Bacillus* bacterium resistant to 8-azaadenine, 2,6-diaminopurine, 6-mercaptopurine, or 6-thioguanine when the activity of the protein is enhanced in the bacterium.

It is a further object of the present invention to provide the bacterium described above, wherein said protein is encoded by a DNA selected from the group consisting of:
(a) a DNA comprising a nucleotide sequence of SEQ ID NO: 1; and
(b) a DNA which is able to hybridize under stringent conditions with a nucleotide sequence complementary to SEQ ID NO: 1 or a probe that can be prepared from the nucleotide sequence of SEQ ID NO: 1, and which encodes a protein having an activity of making an *Escherichia* or *Bacillus* bacterium resistant to 8-azaadenine, 2,6-diaminopurine, 6-mercaptopurine, or 6-thioguanine when said activity of said protein is enhanced in said bacterium.

It is a further object of the present invention to provide the bacterium described above, wherein the stringent conditions comprise washing with 1×SSC, 0.1% SDS, at 60° C.

It is a further object of the present invention to provide the bacterium described above, wherein the activity of the protein as described above is enhanced by transforming the bacterium with a DNA coding for the protein, or by modifying an expression control sequence of said DNA on the chromosome of the bacterium so that the DNA expression is enhanced.

It is a further object of the present invention to provide the bacterium described above, wherein said DNA is present on a multicopy vector.

It is a further object of the present invention to provide the bacterium described above, wherein the purine nucleoside is inosine and/or guanosine.

It is a further object of the present invention to provide a method for producing a purine nucleoside, which comprises cultivating the bacterium described above in a culture medium, and collecting the purine nucleoside from the culture medium.

It is a further object of the present invention to provide the method described above, wherein the bacterium has been modified to have enhanced expression of a gene involved in purine nucleoside biosynthesis.

It is a further object of the present invention to provide the method described above, wherein the purine nucleoside is inosine or guanosine.

It is a further object of the present invention to provide a method for producing a 5'-purine nucleotide, which comprises cultivating the bacterium described above in a culture medium to produce a purine nucleoside, phosphorylating the purine nucleoside to generate a purine nucleotide, and collecting the 5'-purine nucleotide.

It is a further object of the present invention to provide the method described above, wherein the bacterium has been modified to have enhanced expression of a gene involved in purine nucleoside biosynthesis.

It is a further object of the present invention to provide the method described above, wherein the purine nucleoside is inosine and/or guanosine, and the 5'-nucleotide is inosinic acid and/or guanylic acid.

DETAILED DESCRIPTION OF THE PREFERRED EMBODIMENTS

Figure 1:
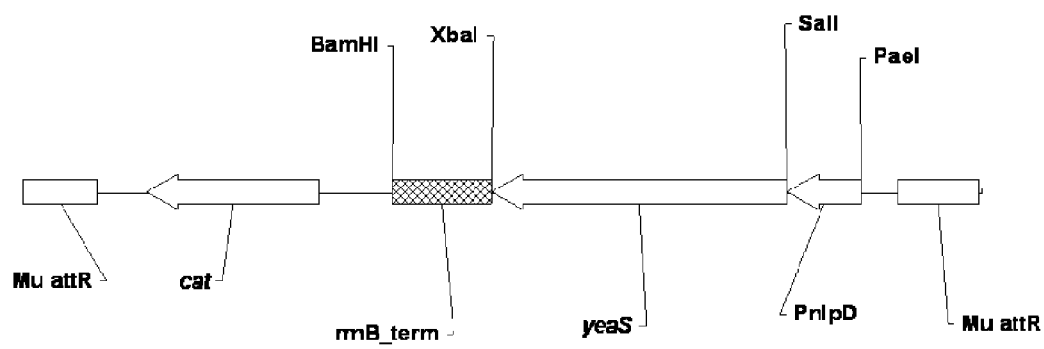
FIG. 1 shows the structure of the PnlpD-yeaS construct.
Figure 2:
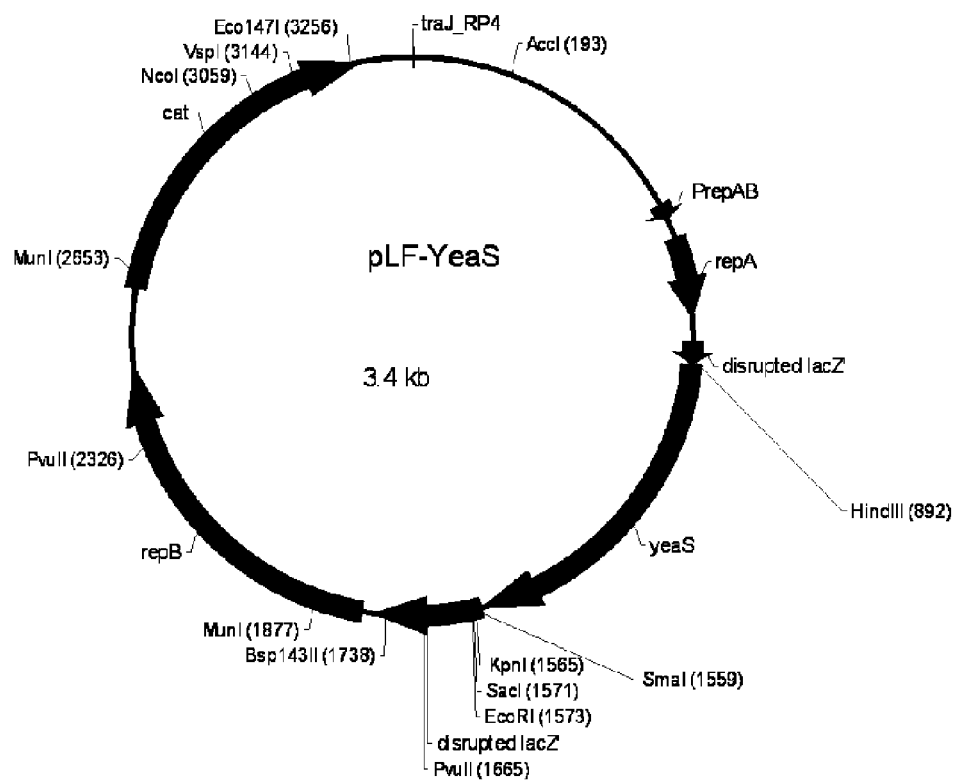
FIG. 2 shows the structure of the pLF-YeaS plasmid

The present invention described in detail below.
1. The Bacterium

Exemplary embodiments of the bacterium of the present invention belong to the genus *Escherichia* or the genus *Bacillus*, the bacterium having the ability to produce purine nucleosides, and wherein an activity of a protein is enhanced. The protein with enhanced activity may have the amino acid sequence shown in SEQ ID NO: 2, or may be a protein of the amino acid sequence shown in SEQ ID NO: 2, but wherein one or several amino acids are substituted, deleted, inserted, added, or inverted. The protein may make the bacterium in which it is expressed resistant to 8-azaadenine, 2,6-diaminopurine, 6-mercaptopurine, or 6-thioguanine. The phrase "a bacterium belonging to the genus *Escherichia* or genus *Bacillus*" or "*Escherichia* or *Bacillus* bacterium" means that the bacterium is classified as the genus *Escherichia* or *Bacillus* according to the classification known to a person skilled in the microbiology. An example of the microorganism belonging to the genus *Escherichia* is *Escherichia coli* (*E. coli*). Examples of the microorganism belonging to the genus *Bacillus* include *Bacillus subtilis*, *Bacillus amyloliquefaciens*, and *Bacillus pumilus*. Examples of *Bacillus subtilis* include *Bacillus subtilis* 168 Marburg strain (ATCC6051) and *Bacillus subtilis* PY79 strain (Plasmid, 1984, 12, 1-9). Examples of *Bacillus amyloliquefaciens* include *Bacillus amyloliquefaciens* T strain (ATCC 23842) and *Bacillus amyloliquefaciens* N strain (ATCC 23845). *Bacillus subtilis* 168 Marburg strain (ATCC6051), *Bacillus amyloliquefaciens* T strain (ATCC 23842) and *Bacillus amyloliquefaciens* N strain (ATCC 23845) can be obtained from American Type Culture Collection (10801 University Boulevard, Manassas, Va., 20110-2209, U.S.A.).

The phrase "purine nucleoside producing ability" means an ability to produce and cause accumulation of inosine, guanosine, xanthosine, or adenosine in a medium. The phrase "having a purine nucleoside producing ability" or "the ability to produce purine nucleosides" means that the microorganism belonging to the genus *Escherichia* or genus *Bacillus* is able to produce and cause accumulation of inosine, guanosine, xanthosine, or adenosine in a medium in amount larger than a wild-type strain of *E. coli*, such as *E. coli* W3110 and MG1655, or a wild-type strain of *B. amyloliquefaciens* such as *B. amyloliquefaciens* K. Preferably, this means that the microorganism is able to produce and cause accumulation in a medium of not less than 10 mg/L, and in another example not less than 50 mg/L of a purine nucleoside such as inosine, guanosine, xanthosine, or adenosine.

The phrase "an activity of a protein is enhanced" means that the number of molecules of the protein in a cell is increased, or that the activity per protein molecule is increased. The term "activity" means that the bacterium becomes resistant to 8-azaadenine, 2,6-diaminopurine, 6-mercaptopurine, or 6-thioguanine when the activity is enhanced in the bacterium as compared to a strain in which the activity is not enhanced.

Exemplary proteins of the present invention include those defined as follows:
(A) a protein having the amino acid sequence shown in SEQ ID NO: 2, and
(B) a protein having the amino acid sequence shown in SEQ ID NO:2, wherein one or several amino acids are substituted, deleted, inserted, added, or inverted, and the protein has an activity of making the bacterium resistant to 8-azaadenine, 2,6-diaminopurine, 6-mercaptopurine, or 6-thioguanine. The protein may be called the YeaS protein. The YeaS protein is a highly hydrophobic protein which typically consists of 212 amino acids, and contains 6 predicted transmembrane segments, however the function of this protein is unknown (ecocyc.org, www.tcdb.org). The YeaS protein is coded for by the yeaS gene. The yeaS gene (numbers 1878145 to 1878783 in the sequence of GenBank accession NC_000913) is located on the *E. coli* chromosome between the yeaR and yeaT genes. The yeaS (now renamed as leuE) gene may encode a protein which is involved in amino acid export (Russian patent No. 2175351; Aleshin et al., TIBS, 1999; Kutukova et al., FEBS Letters, 579, 4629-4534, 2005).

The number of amino acids which may be deleted, substituted, inserted, or added can differ depending on the position in the three-dimensional structure of the protein or the type of amino acid. It may be 1 to 27, for example, and in another example, 1 to 15, and in another example 1 to 5 for the protein shown in SEQ ID NO: 2.

The phrase "enhanced resistance to 8-azaadenine, 2,6-diaminopurine, 6-mercaptopurine, or 6-thioguanine" means that the bacterium can grow on a minimal medium containing 8-azaadenine, 2,6-diaminopurine, 6-mercaptopurine, or 6-thioguanine at concentrations that the wild-type or parental strain cannot grow. This phrase may also mean that the bacterium can grow on a medium containing 8-azaadenine, 2,6-diaminopurine, 6-mercaptopurine, or 6-thioguanine faster than the wild-type or parental strain of the bacterium. The concentration of the purine base analogues is generally 10 to 5000 µg/ml, preferably 50 to 1000 µg/ml.

Techniques for enhancing the activity of the protein, especially techniques for increasing the number of protein molecules in a cell, include, but are not limited to, altering an expression regulatory sequence of the DNA coding for the protein, and/or increasing the copy number of the gene.

Altering an expression regulatory sequence of the DNA coding for the protein of present invention can be achieved by placing the DNA under the control of a potent promoter. For example, the lac promoter, trp promoter, promoter of nlpD gene, trc promoter, $P_L$ promoter of lambda phage, and the promoter of the repA gene on the pLF22 plasmid are known as potent promoters. Alternatively, the promoter can be enhanced by, for example, introducing a mutation into the promoter which results in an increase in the transcription level of a structural gene located downstream of the promoter. Furthermore, the mRNA translatability can be enhanced by introducing a mutation into the spacer region between the ribosome binding site (RBS) and the start codon. For example, a 20-fold range in the expression levels was found, depending on the nature of the three nucleotides preceding the start codon (Gold et al., Annu. Rev. Microbiol., 35, 365-403, 1981; Hui et al., EMBO J., 3, 623-629, 1984). Besides, the expression of the DNA coding for the protein in cells of *Bacillus* can be achieved by placing the DNA under a RBS specific for *Bacillus*, for example, the RBS of the *B. subtilis* purE gene (see Example 4).

Furthermore, to increase the transcription level of the gene, an enhancer may be introduced. Introduction of DNA containing either the gene or promoter into the chromosome is described in, for example, Japanese Patent Application Laid-Open No. 1-215280 (1989).

Alternatively, the copy number of the gene may be increased by inserting the gene into a multi-copy vector, followed by introducing the vector into a microorganism. Vectors which can be used include *E. coli* plasmid vectors such as pMW118, pBR322, pUC19, pBluescript KS+, pACYC177, pACYC184, pAYC32, pMW119, pET22b, *E. coli-B. subtilis* shuttle vectors such as pHY300PLK, pGK12, pLF14, pLF22, or the like, phage vectors such as 11059, 1BF101, M13 mp9, Mu phage (Japanese Patent Application Laid-Open No. 2-109985), or the like, and transposons (Berg, D. E. and Berg, C. M., Bio/Technol., 1, 417 (1983)), such as Mu, Tn10, Tn5, or the like. It is also possible to increase the copy number of a gene by integrating the gene into a chromosome by homologous recombination utilizing a plasmid, a transposon, or the like.

The technique of using the potent promoter or enhancer can be combined with the technique based on the multiplication of gene copies.

Methods for preparation of chromosomal DNA, hybridization, PCR, preparation of plasmid DNA, digestion and ligation of DNA, transformation, selection of an oligonucleotide as a primer, and the like may be ordinary methods well known to one skilled in the art. These methods are described in Sambrook, J., and Russell D., "Molecular Cloning A Laboratory Manual, Third Edition", Cold Spring Harbor Laboratory Press (2001), and the like.

To breed a microorganism belonging to the genus *Escherichia* which has increased expression of the gene coding for an exemplary protein of the present invention, necessary regions of genes may be obtained by PCR (polymerase chain reaction) based on available information about *E. coli* genes. For example, the yeaS gene, which appears to code for a transporter, can be cloned from the chromosomal DNA of *E. coli* K12 W3110 or *E. coli* MG1655 using PCR. The chromosomal DNA may be derived or obtained from any other strain of *E. coli*.

Exemplary proteins of the present invention include mutants and variants of the YeaS protein which exist due to natural diversity, provided that the mutants and variants still possess the functional property of the YeaS protein, that is, are at least able to confer resistance to 8-azaadenine, 2,6-diaminopurine, 6-mercaptopurine, or 6-thioguanine. The DNA coding for the mutants and variants can be obtained by isolating DNA which hybridizes with DNA complementary to the yeaS gene (SEQ ID NO: 1), or a part of the gene under stringent conditions, and which codes for a protein which enhances purine nucleoside production. The term "stringent conditions" means conditions under which so-called specific hybrids form, and non-specific hybrids do not form. For example, stringent conditions include conditions under which DNAs having high homology, for instance DNAs having homology no less than 70%, 80%, 90% or 95%, hybridize to each other. Alternatively, the stringent conditions are exemplified by conditions which are ordinary conditions of washing in Southern hybridization, e.g., 60° C., 1×SSC, 0.1% SDS, or in another example, 0.1×SSC, 0.1% SDS, or in another example 65° C., 0.1×SSC, 0.1% SDS. As a probe for the DNA which codes for variants and hybridizes with the yeaS gene, a partial sequence of the nucleotide sequence of SEQ ID NO: 1 can also be used. Such a probe may be prepared by PCR using oligonucleotides produced based on the nucleotide sequence of SEQ ID NO: 1 as primers, and a DNA fragment containing the nucleotide sequence of SEQ ID NO: 1 as a template. When a DNA fragment having a length of about 300 bp is used as the probe, the conditions of washing for hybridization can be, for example, 50° C., 2×SSC, and 0.1% SDS.

So long as the activity of the YeaS protein is maintained, YeaS may have the amino acid sequence of SEQ ID NO: 2, wherein one or several amino acids are substituted, deleted, inserted, or added at one or multiple positions. Herein, although the term "several" depends on the type and position of the amino acid residues within the three dimensional structure of the protein; it means 1 to 27, or in another example 1 to 15, and in another example, 1 to 5.

The above-described mutation in the amino acid sequence of SEQ ID NO: 2 is preferably a conservative mutation which does not impair the activity of the protein. A substitution means a mutation whereby at least one residue in the amino acid sequence is removed and one or more residues are inserted at that location. Conservative substitutions include: substitution of Ala with Ser or Thr, substitution of Arg with Gln, His, or Lys, substitution of Asn with Glu, Gln, Lys, His, or Asp, substitution of Asp with Asn, Glu, or Gln, substitution of Cys with Ser or Ala, substitution of Gln with Asn, Glu, Lys, His, Asp, or Arg, substitution of Glu with Gly, Asn, Gln, Lys, or Asp, substitution of Gly with Pro, substitution of His with Asn, Lys, Gln, Arg, or Tyr, substitution of Ile with Leu, Met, Val, or Phe, substitution of Leu with Ile, Met, Val, or Phe, substitution of Lys with Asn, Glu, Gln, His, or Arg, substitution of Met with Ile, Leu, Val, or Phe, substitution of Phe with Trp, Tyr, Met, Ile, or Leu, substitution of Ser with Thr or Ala, substitution of Thr with Ser or Ala, substitution of Trp with Phe or Tyr, substitution of Tyr with His, Phe, or Trp, and substitution of Val with Met, Ile, or Leu.

Exemplary bacteria of the present invention can be obtained by enhancing the activity of an exemplary protein of present invention in a bacterium which has a native ability to produce a purine nucleoside. Alternatively, the bacterium can be obtained by imparting the ability to produce a purine nucleoside to a bacterium which already has enhanced activity of the protein.

The parent strain which produces purine nucleosides and is to be enhanced in the activities of the proteins of the present invention may be the *E. coli* strain FADRaddedd(pMWKQ) (WO99/03988). This strain is a derivative of the known strain W3110, which has mutations introduced into the purF gene coding for PRPP amidotransferase, purR gene coding for a purine repressor, deoD gene coding for purine nucleoside phosphorylase, purA gene coding for succinyl-AMP synthase, add gene coding for adenosine deaminase, edd gene coding for 6-phosphogluconate dehydratase (WO9903988), and which contains the pMWKQ plasmid containing the purFKQ gene coding for the PRPP amidotransferase which is insensitive to GMP (WO9903988).

An example of the parent strain belonging to the genus *Bacillus* is the *B. subtilis* strain KMBS16-1. This strain is a derivative of the inosine producing strain *B. subtilis* KMBS16 (US2004-0166575), in which a purA::erm mutation was changed to a purA::cat mutation. In turn, *B. subtilis* KMBS16 is a derivative of the known *B. subtilis* trpC2, which has mutations introduced into the purA gene coding for succinyl-AMP synthase (purA::erm), the purR gene coding for a purine repressor (purR::spc), and the deoD gene coding for purine nucleoside phosphorylase (deoD::kan) (Russian patent No. 2239656). Other parent strains belonging to the genus *Bacillus* include the inosine-producing bacterial strains belonging to the genus *Bacillus*, such as *Bacillus subtilis* strain AJ12707 (FERM P-12951) (Japanese patent application JP6113876), *Bacillus subtilis* strain AJ3772 (FERM-P 2555) (Japanese patent application JP62014794), *Bacillus pumilus* NA-1102 (FERM BP-289), *Bacillus subtilis* NA-6011 (FERM BP-291), "*Bacillus subtilis*" G1136A (U.S. Pat. No. 3,575,809), which was deposited on Mar. 10, 2005 at the VKPM (the Russian National Collection of Industrial Microorganisms, Russia, 117545 Moscow, 1 Dorozhny proezd, 1) as *Bacillus amyloliquefaciens* AJ1991 (VKPM B-8994, WO2005095627), *Bacillus subtilis* NA-6012 (FERM BP-292) (U.S. Pat. No. 4,701,413), *B. pumilis* Gottheil No. 3218 (ATCC No. 21005) (U.S. Pat. No. 3,616,206), *B. amyloliquefaciens* strain AS115-7 (VKPM B-6134) (Russian patent No. 2003678), or the like.

To increase the activity per protein molecule, it is also possible to introduce a mutation into the structural gene of the protein to increase the specific activity of the protein encoded by the gene. In order to introduce a mutation into a gene, site-specific mutagenesis (Kramer, W. and Frits, H. J., Methods in Enzymology, 154, 350 (1987)), recombinant PCR (PCR Technology, Stockton Press (1989)), chemical synthesis of a specific portion of DNA, hydroxylamine treatment of a gene of interest, treatment of microbial strains having a gene of interest by UV irradiation or a chemical agent such as nitrosoguanidine or nitrous acid, and the like can be used. A microorganism in which the activity of the protein is enhanced can be selected by growing candidates strains in a minimal medium containing concentrations of 8-azaadenine, 2,6-diaminopurine, 6-mercaptopurine, or 6-thioguanine at which a non-modified or wild-type strain cannot grow. Alternatively, a microorganism in which the activity of the protein is enhanced can be selected by identifying strains which grow faster in a medium containing 8-azaadenine, 2,6-diaminopurine, 6-mercaptopurine, or 6-thioguanine than a non-modified or wild-type strain of the microorganism.

The bacterium may be further improved by enhancing the expression of one or more genes involved in purine biosynthesis. Such genes include the pur regulon of *E. coli* (*Escherichia coli* and *Salmonella*, Second Edition, Editor in Chief: F. C. Neidhardt, ASM Press, Washington D.C., 1996), or the pur-operon of *B. subtilis* (*Bacillus subtilis* and other Gram-positive bacteria. Editor in Chief: A. L. Sonenshein. ASM Press, Washington D.C., 1993). The inosine-producing *E. coli* strain having a mutant purF gene encoding a PRPP amidotransferase which is not subject to feedback inhibition by GMP and AMP, and an inactivated purR gene encoding the repressor in the purine nucleotide biosynthesis system, has been described (WO9903988).

The mechanism of enhanced purine nucleoside production by a bacterium by enhancing an activity of an exemplary protein of the present invention may be a result of increased excretion of the target purine nucleoside.

2. Method for Producing Purine Nucleoside Such as Inosine and/or Guanosine

Exemplary methods of the present invention include a method for producing a nucleoside such as inosine and/or guanosine, and includes the steps of cultivating an exemplary bacterium of the present invention in a culture medium to allow production and subsequent accumulation of the nucleoside in the culture medium, and collecting the nucleoside from the culture medium.

The cultivation, collection, and purification of purine nucleosides from the medium and the like may be performed in a manner similar to conventional fermentation methods wherein a purine nucleoside is produced using a microorganism. The culture medium for purine nucleoside production may be a typical medium which contains a carbon source, a nitrogen source, inorganic ions, and other organic components as required. As the carbon source, saccharides such as glucose, lactose, galactose, fructose, arabinose, maltose, xylose, trehalose, ribose and hydrolyzates of starches; alcohols such as glycerol, mannitol and sorbitol; organic acids such as gluconic acid, fumaric acid, citric acid and succinic acid and the like can be used. As the nitrogen source, inorganic ammonium salts such as ammonium sulfate, ammonium chloride, and ammonium phosphate; organic nitrogen such as of soybean hydrolyzates; ammonia gas; aqueous ammonia, and the like can be used. It is desirable that vitamins such as vitamin B1, required substances, for example, organic nutrients such as nucleic acids such as adenine and RNA, or yeast extract, and the like may be present in appropriate, or even trace, amounts. Other than these, small amounts of calcium phosphate, magnesium sulfate, iron ions, manganese ions, and the like may be added, if necessary.

Cultivation is preferably performed under aerobic conditions for 16 to 72 hours, the culture temperature during cultivation is preferably controlled to within 30 to 45° C., and the pH is preferably controlled to within 5 to 8. The pH can be adjusted by using an inorganic or organic acidic or alkaline substance, as well as ammonia gas.

After cultivation, solids such as cells can be removed from the liquid medium by centrifugation or membrane filtration, and then the target purine nucleoside can be recovered from the fermentation liquor by any combination of conventional techniques such as by using an ion exchange resin and precipitation.

3. Method for Producing Purine Nucleotides Such as 5'-Inosinic Acid and/or 5'-Guanylic Acid Exemplary methods of the present invention include a method for producing purine nucleotides which includes the steps of cultivating an exemplary bacterium of the present invention in a culture medium to produce a purine nucleoside, and phosphorylating the purine nucleoside to generate the 5'-purine nucleotide, and collecting the 5'-purine nucleotide.

The phrase "5'-purine nucleotide" includes 5'-inosinic acid, 5'-guanylic acid, 5'-xanthylic acid, and 5'-adenylic acid, preferably 5'-inosinic acid and/or 5'-guanylic acid. Inosine, xanthosine, guanosine, and adenosine are phosphorylated to generate 5'-inosinic acid, 5'-guanylic acid, 5'-xanthylic acid, and 5'-adenylic acid.

The cultivation, collection, and purification of purine nucleosides such as inosine and/or guanosine from the medium, and the like, may be performed in a manner similar to conventional fermentation methods wherein inosine and/or guanosine is produced using a microorganism. Furthermore, phosphorylating a purine nucleoside such as inosine and/or guanosine, and collecting 5'-purine nucleotides inosinic acid and/or 5'-guanylic acid may be performed in a manner similar to conventional fermentation methods wherein a purine nucleotide such as 5'-inosinic acid and/or 5'-guanylic acid is produced from a purine nucleoside such as inosine and/or guanosine.

The phosphorylation of the purine nucleoside may be performed enzymatically using different phosphatases, nucleoside kinases, or nucleoside phosphotransferases, or may be performed chemically using phosphorylating agents such as $POCl_3$, or the like. A phosphatase may be used which is able to catalyze the selective transfer of a phosphoryl group at the C-5' position of a pyrophosphate to a nucleoside (Mihara et. al, Phosphorylation of nucleosides by the mutated acid phosphatase from *Morganella morganii*. Appl. Environ. Microbiol. 2000, 66:2811-2816). An acid phosphatase which utilizes poly-phosphoric acid (salts), phenylphosphoric acid (salts), or carbamylphosphoric acid (salts) as a phosphoric acid donor (WO9637603A1), or the like, may also be used. Also, a phosphatase which is able to catalyze the transfer of a phosphoryl group to the C-2', 3', or 5'-position of a nucleoside utilizing p-nitrophenyl phosphate (Mitsugi, K., et al, Agric. Biol. Chem. 1964, 28, 586-600), inorganic phosphate (JP 42-1186), or acetyl phosphate (JP 61-41555) as a substrate, or the like, may be used. The guanosine/inosine kinase from *E. coli* (Mori et. al. Cloning of a guanosine-inosine kinase gene of *Escherichia coli* and characterization of the purified gene product. J. Bacteriol. 1995. 177:4921-4926; WO9108286), or the like, may be used. The nucleoside phosphotransferases described by Hammer-Jespersen, K. (Nucleoside catabolism, p. 203-258. In A Munch-Petesen (ed.), Metabolism of nucleotides, nucleosides, and nucleobases in microorganism. 1980, Academic Press, New York), or the like, may be used. Chemical phosphorylation of a nucleoside may be performed using a phosphorylation agent such as $POCl_3$ (Yoshikawa et. al. Studies of phosphorylation. III. Selective phosphorylation of unprotected nucleosides. Bull. Chem. Soc. Jpn. 1969, 42:3505-3508), or the like.

In an exemplary method of the present invention, the bacterium may also be modified to have enhanced expression of a gene involved in purine nucleoside biosynthesis.

EXAMPLES

Example 1

Cloning of the yeaS Gene Under the Potent Constitutive $P_{nlpD}$ Promoter and Integration of the Cloned Construct into the Chromosome The entire nucleotide sequence of *E. coli* strain K-12 has been reported (Science, 277, 1453-1474, 1997). A PSI-BLAST search revealed that at least 4 rhtB paralogues, including the yeaS gene, are present in the genome of *E. coli* K-12. The yeaS gene encodes a transmembrane protein of unknown function.

Based on the reported nucleotide sequence, the primers depicted in SEQ ID NO: 3 (primer 1) and SEQ ID NO: 4 (primer 2) were synthesized. The chromosomal DNA of *E. coli* strain MG1655 was prepared by an ordinary method. PCR was carried out on "Perkin Elmer GeneAmp PCR System 2400" under the following conditions: 40 sec. at 95° C., 40 sec. at 47° C., 40 sec. at 72° C., 30 cycles by means of Taq polymerase (Fermentas). The PCR fragment was digested with SalI and XbaI, and cloned into the SalI and XbaI sites of plasmid pMIV-$P_{nlpD}$ and placed under the control of the *E. coli* nlpD gene promoter. pMIV-$P_{nlpD}$ was obtained by the consecutive cloning of the cat gene, promoter, and RBS of the nlpD gene encoding the predicted outer membrane lipoprotein between the Mu-phage attachment sites of pM1 (Russian patent No. 2212447, Kutukova et al., FEBS Letters, 579, 4629-44634, 2005). Integration of this cat-$P_{nlpD}$-yeaS cassette (FIG. 1) into the chromosome of *E. coli* TG1 (K12, del(lac-pro), supE, thi, hsdD5/F' traD36, proA+B+, lacIq, lacZdelM15) was performed with the Mu integration system using the helper plasmid pMH10, as described in Russian patent No. 2212447. The *E. coli* TG1 stain can be obtained from DSMZ (German Collection of Microorganisms and Cell Cultures, Inhoffenstrasse 7B, 38124, Braunschweig, Germany).

Thus, the strain TG1::$P_{nlpD}$-yeaS was obtained.

Example 2

Effect of yeaS Gene Overexpression on the Resistance of *E. coli* Strain TG1 to Purine Base Analogues The minimal inhibitory concentrations (MIC) of purine base analogues for the strain TG1::$P_{nlpD}$-yeaS and the parental strain TG1 were determined on M9 glucose minimal agar plates containing graded concentrations of inhibitors. The plates were spotted with $10^5$ to $10^6$ cells from an overnight culture grown in a minimal medium. The growth was estimated after 44 h incubation at 37° C. The results are presented in Table 1.

As seen from Table 1, the overexpression of the yeaS gene increased the cells' resistance to 8-azaadenine, 2,6-diaminopurine, 6-mercaptopurine, and 6-thioguanine. The yeaS (leuE) gene is known to encode a membrane protein involved in efflux of amino acids (Russian patent No. 2175351; Aleshin et al., TIBS, 1999; Kutukova et al., FEBS Letters, 579, 4629-4534, 2005). Therefore, the YeaS protein has a broad specificity and is also involved in the excretion of purine derivatives.

TABLE 1

|  | MIC (μg/ml) for *E. coli* strain | |
| --- | --- | --- |
| Substrate | TG1 | TG1::$P_{nlpD}$-yeaS |
| 8-azaadenine | 100 | 250 |
| 2,6-diaminopurine | 200 | 600 |
| 6-mercaptopurine | 50 | 150 |
| 6-thioguanine | 30 | 450 |

Example 3

Effect of yeaS Gene Overexpression on Inosine Production by the *E. coli* Inosine Producing Strain The inosine producing strain *E. coli* FADRaddedd(pMWKQ)(WO99/03988) was transduced by phage P1 grown on the TG1::$P_{nlpD}$-yeaS strain. Transductants were selected on LB agar containing 10 μg/ml chloramphenicol and 75 μg/ml kanamycin. Thus, the strain *E. coli* FADRaddedd::$P_{nlpD}$-yeaS (pMWKQ) was obtained. This strain and the parent strain *E. coli* FADRaddedd(pMWKQ) were each cultivated at 37° C. for 18 hours in L-broth with 75 μg/ml kanamycin, and 0.3 ml of the culture was inoculated into 3 ml of a fermentation medium containing 75 mg/l kanamycin, in a 20×200 mm test tube, and cultivated at 37° C. for 72 hours with a rotary shaker.

The composition of the fermentation medium (g/l):

| Glucose | 40.0 |
| --- | --- |
| (NH$_4$)$_2$SO$_4$ | 16.0 |
| K$_2$HPO$_4$ | 1.0 |
| MgSO$_4$•7H$_2$O | 1.0 |
| FeSO$_4$•7H$_2$O | 0.01 |
| MnSO$_4$•5H$_2$O | 0.01 |
| Yeast extract | 8.0 |
| CaCO$_3$ | 30.0 |

Glucose and magnesium sulfate are sterilized separately. CaCO$_3$ dry-heat sterilized at 180° C. for 2 h. pH is adjusted to 7.0. The antibiotic is introduced into the medium after sterilization.

After the cultivation, the amount of inosine which accumulated in the medium was determined by HPLC. A sample of the culture medium (500 μl) is centrifuged at 15,000 rpm for 5 minutes, and the supernatant is diluted 4 times with H$_2$O and analyzed by HPLC.

Conditions for HPLC analysis: Column: Luna C18(2) 250×3 mm, 5u (Phenomenex, USA). Buffer: 2% v/v C$_2$H$_5$OH; 0.8% v/v thriethylamine; 0.5% v/v acetic acid (glacial); pH 4.5. Temperature: 30° C. Flow rate: 0.3 ml/min. Injection volume: 5 μl.

Detection: UV 250 nm.
Retention Time (Min):

| Xanthosine | 13.7 |
| --- | --- |
| Inosine | 9.6 |
| Guanosine | 11.4 |
| Adenosine | 28.2 |

The results are presented in Table 2.

TABLE 2

| Strain | OD$_{540}$ | Inosine, g/l |
| --- | --- | --- |
| *E. coli* FADRaddedd(pMWKQ) | 8.0 | 1.24 |
| *E. coli* FADRaddedd::_$P_{nlpD}$-yeaS (pMWKQ) | 7.7 | 1.69 |

As seen from Table 2, yeaS gene overexpression improved inosine productivity of the FADRaddedd(pMWKQ) strain.

Example 4

Cloning of the yeaS Gene into the Single Replicon Shuttle Vector pLF22

To express the yeaS gene in *Bacillus* strains, the gene was cloned into the single replicon shuttle vector pLF22 (Tarakanov et al., Expression vector pLF22 for the lactic acid bacteria. Mikrobiologiia (Rus). 73(2), 211-217, (2004)) under the control of the repAB genes' promoter present on the plasmid and the ribosome-binding site of the purE gene of *Bacillus subtilis*. For this purpose, the primers 3 (SEQ ID NO: 5) and 4 (SEQ ID NO: 6) were used in PCR with the chromosomal DNA of MG1655 as a template. Primer 3 contains the ribosome-binding site of the *B. subtilis* purE gene. The resulting fragment was digested with SmaI and HindIII, and cloned into the SmaI and HindIII sites of plasmid pLF22 under the control of the repAB genes promoter. Thus, the plasmid pLF-YeaS was obtained.

Example 5

Effect of the yeaS Gene Overexpression on Inosine and Guanosine Production by the *Bacillus amyloliquefaciens* Inosine-Guanosine Producing Strain The plasmids pLF22 and pLF-YeaS were introduced into *B. subtilis* 168 strain by transformation, and the transformants were named *B. subtilis* (pLF22) and *B. subtilis* (pLF-YeaS), respectively. Then, the phage E40 grown on these strains was used to transduce the strain *B. amyloliquefaciens* AJ1991 (ATCC No. 19222, VKPM B-8994)(U.S. Pat. No. 3,575, 809). Transductants were selected on LB containing 10 μg/ml chloramphenicol. Thus, the strains *B. amyloliquefaciens* AJ1991(pLF22) and *B. amyloliquefaciens* AJ1991(pLF-YeaS) were obtained.

The strain *B. amyloliquefaciens* AJ1991(pLF-YeaS) and the control strain *B. amyloliquefaciens* AJ1991(pLF22) were each cultivated at 34° C. for 18 hours in L-broth. Then, 0.3 ml of the culture was inoculated into 3 ml of the fermentation medium in 20×200 mm test tubes, and cultivated at 34° C. for 72 hours with a rotary shaker.

The composition of the fermentation medium is as follows:
(g/l)

| | |
|---|---|
| Glucose | 80.0 |
| $KH_2PO_4$ | 1.0 |
| $MgSO_4$ | 0.4 |
| $FeSO_4 \cdot 7H_2O$ | 0.01 |
| $MnSO_4 \cdot 5H_2O$ | 0.01 |
| $NH_4Cl$ | 15.0 |
| Adenine | 0.3 |
| Total nitrogen (in the form of Mameno*) | 0.8 |
| $CaCO_3$ | 25.0 |

*soybean hydrolysate

Glucose and magnesium sulfate are sterilized separately. $CaCO_3$ is dry-heat sterilized at 180° for 2 h. The pH is adjusted to 7.0.

After the cultivation, the amount of inosine and guanosine that accumulated in the medium was determined by HPLC as above. The results are presented in Table 3.

TABLE 3

| Strain | $OD_{540}$ | Inosine, g/l | Guanosine, g/l |
|---|---|---|---|
| B. amyloliquefaciens AJ1991 (pLF22) | 8.4 | 1.2 | 1.12 |
| B. amyloliquefaciens AJ1991(pLF-YeaS) | 9.2 | 2.2 | 1.5 |

It follows from the Table 3, that overexpression of the yeaS gene improved inosine and guanosine productivity of the *B. amyloliquefaciens* AJ1991(pLF-YeaS) strain.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

INDUSTRIAL APPLICABILITY

According to the present invention, the production of a purine nucleoside by an *Escherichia* or *Bacillus* bacterium can be enhanced. Produced purine nucleoside can be used to, for example, produce 5'-purine nucleotide.

The invention claimed is:

1. A method for producing a purine nucleoside comprising cultivating a bacterium of the genus *Escherichia* or *Bacillus* having a purine nucleoside producing ability in a culture medium, and collecting from the culture medium the purine nucleoside, wherein an activity of YeaS protein is enhanced in the bacterium, the YeaS protein is selected from the group consisting of:

A) a protein comprising the amino acid sequence shown in SEQ ID NO: 2; and

B) a protein comprising the amino acid sequence shown in SEQ ID NO: 2, wherein one to five amino acids are substituted, deleted, inserted, added, or inverted, and the protein has the activity of YeaS protein, wherein the activity is making the *Escherichia* or *Bacillus* bacterium resistant to 8-azaadenine, 2,6-diaminopurine, 6-mercaptopurine, or 6-thioguanine.

2. The method according to claim 1, wherein the bacterium has been modified to have enhanced expression of a gene involved in purine nucleoside biosynthesis.

3. The method according to claim 1, wherein the purine nucleoside is inosine or guanosine.

4. The method according to claim 1, wherein the activity of the protein is enhanced by transforming the bacterium with a DNA coding for the protein, or by modifying an expression control sequence of a DNA coding for the protein on the chromosome of the bacterium so that the expression of the DNA coding for the protein is enhanced, wherein said DNA comprises the nucleotide sequence of SEQ ID NO: 1.

5. The method according to claim 4, wherein said DNA is located on a multicopy vector.

6. A method for producing a 5'-purine nucleotide comprising cultivating a bacterium of the genus *Escherichia* or *Bacillus* having a purine nucleoside producing ability in a culture medium to produce a purine nucleoside, phosphorylating the purine nucleoside to generate a purine nucleotide, and collecting the 5'-purine nucleotide, wherein an activity of YeaS protein is enhanced in the bacterium, the YeaS protein is selected from the group consisting of:

A) a protein comprising the amino acid sequence shown in SEQ ID NO: 2; and

B) a protein comprising the amino acid sequence shown in SEQ ID NO: 2, wherein one to five amino acids are substituted, deleted, inserted, added, or inverted, and the protein has the activity of YeaS protein, wherein the activity is the activity of making the *Escherichia* or *Bacillus* bacterium resistant to 8-azaadenine, 2,6-diaminopurine, 6-mercaptopurine, or 6-thioguanine.

7. The method according to claim 6, wherein the bacterium has been modified to have enhanced expression of a gene involved in purine nucleoside biosynthesis.

8. The method according to claim 6, wherein the purine nucleoside is inosine and/or guanosine, and the 5'-nucleotide is inosinic acid and/or guanylic acid.

9. The method according to claim 6, wherein the activity of the protein is enhanced by transforming the bacterium with a DNA coding for the protein, or by modifying an expression control sequence of a DNA coding for the protein on the chromosome of the bacterium so that the expression of the DNA coding for the protein is enhanced, wherein said DNA:

10. The method according to claim 9, wherein said DNA is located on a multicopy vector.

* * * * *

UNITED STATES PATENT AND TRADEMARK OFFICE
CERTIFICATE OF CORRECTION

PATENT NO. : 8,034,767 B2
APPLICATION NO. : 12/476476
DATED : October 11, 2011
INVENTOR(S) : Kutukova et al.

It is certified that error appears in the above-identified patent and that said Letters Patent is hereby corrected as shown below:

Column 18, Claim 6, line 47, cancel the text beginning with "Claim 6. A method" to "or 6-thioguanine" at column 18, line 59 and insert the following claim:

--6. A method for producing a 5'-purine nucleotide comprising cultivating a bacterium of the genus Escherichia or Bacillus having a purine nucleoside producing ability in a culture medium to produce a purine nucleoside, phosphorylating the purine nucleoside to generate a 5'-purine nucleotide, and collecting the 5'-purine nucleotide, wherein an activity of YeaS protein is enhanced in the bacterium, the YeaS protein is selected from the group consisting of:
    A) a protein comprising the amino acid sequence shown in SEQ ID NO: 2; and
    B) a protein comprising the amino acid sequence shown in SEQ ID NO: 2, wherein one to five amino acids are added and the protein has the activity of YeaS protein, wherein the activity is the activity of making the Escherichia or Bacillus bacterium resistant to 8-azaadenine, 2,6-diaminopurine, 6-mercaptopurine, or 6-thioguanine.--

Column 19, Claim 8, line 1, cancel the text beginning with "8. The method" to "and/or guanylic acid." at column 19, line 3 and insert the following claim:

--8. The method according to claim 6, wherein the purine nucleoside is inosine and/or guanosine, and the 5'-purine nucleotide is inosinic acid and/or guanylic acid.--

Signed and Sealed this
Third Day of July, 2012

David J. Kappos
*Director of the United States Patent and Trademark Office*